US00PP32587P2

(12) United States Plant Patent
Hansen

(10) Patent No.: US PP32,587 P2
(45) Date of Patent: Dec. 8, 2020

(54) ***HIBISCUS* PLANT NAMED 'CANDY CRUSH'**

(50) Latin Name: ***Hibiscus* hybrid (L.)**
Varietal Denomination: Candy Crush

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,782

(22) Filed: Nov. 26, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu

(57) ABSTRACT

A new and distinct cultivar of winter-hardy, herbaceous, perennial, hybrid *Hibiscus* plant named 'Candy Crush' comprising an upright mounded habit of multiple, well-branched, basal stems producing flowers from the bottom to the top of the plant from late July to early September. Flowers have overlapping petals of bubblegum-pink with slightly darker veins and dark red shiny eye with leading margin folded underneath giving flowers extra strength and resistance to wind damage. The foliage is three- to five-lobed, and rich bright-green.

1 Drawing Sheet

Botanical classification: *Hibiscus* hybrid (L.).
Variety denomination: 'Candy Crush'.

STATEMENT REGARDING PRIOR DISCLOSURES UNDER 37 CFR 1.77(B)(6)

The first publically released photograph of the new plant was on Dec. 1, 2018 when it was displayed with a photograph and brief non-enabling description on the website operated by Walters Gardens, Inc. The first disclosure, in the form of a sale, was made by Walters Gardens, Inc. on Apr. 1, 2019. Walters Gardens, Inc. obtained the new plant and all information relating thereto, from the inventor. No plants of *Hibiscus* 'Candy Crush' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Candy Crush' hybridized under direction of the inventor Aug. 17, 2015 at a wholesale perennial nursery in Zeeland, Mich. The new plant is a hybrid of the unreleased, proprietary hybrid known as 12-312-11 (not patented) times the unreleased, proprietary hybrid known as 12-165-2 (not patented). Into the trial process the new plant was assigned the breeder code labeled 15-95-202. Both parents have a complex mixture of species in them, comprising the species: moscheutos and coccineus.

*Hibiscus* 'Candy Crush' was first asexually propagated in late summer of 2017 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Candy Crush' differs from its parents as well as all other hardy herbaceous *Hibiscus* known to the applicant in many traits. The most similar *Hibiscus* known to the applicant are: 'Jazzberry Jam' (not patented), 'Evening Rose' copending U.S. Plant patent application Ser. No. 16/602,618, 'Cranberry Crush' U.S. Plant Pat. No. 21,984 and 'Berry Awesome' U.S. Plant Pat. No. 27,936. 'Jazzberry Jam' has a much taller habit with flower petals that are deeper pinkish-magenta with more folding. 'Evening Rose' has a slightly taller habit, more burgundy tinted foliage with flowers that are vivid purplish-red and more folded. 'Cranberry Crush' has a similar upright habit with deeper scarlet-red flower that is slightly more cupped. 'Berry Awesome' has a slightly shorter habit rounded habit with flowers that are more lavender pink. 'Pink Elephant' U.S. Plant Pat. No. 21,883 has a much taller habit with larger and lighter pink flowers. 'Sweet Caroline' U.S. Plant Pat. No. 7,608 has a flower with lighter pink exterior and lighter red eye. 'Party Favor' U.S. Plant Pat. No. 22,250 has a lighter pink flower and more open, less upright habit.

The female parent has flowers that are more cupped with petals that are near white with a light blush of red toward the perimeter of the petals and a red eye. Comparison with the male parent is not possible as neither photographs nor plants were maintained.

*Hibiscus* 'Candy Crush' is a unique hardy herbaceous *Hibiscus* with the following combined traits:

1. Winter-hardy compact perennial with upright mounded habit of multiple, well-branched, basal stems;

2. Many rotate flowers of bubblegum-pink with slightly darker veins and dark shiny red eye produced from bottom to top of plant;
3. Petals are overlapping with the leading edge folded underneath giving extra strength and resistance to wind damage;
4. Flowers produced over a long period from late July to early September.
5. Three to five-lobed foliage of rich bright green color;

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
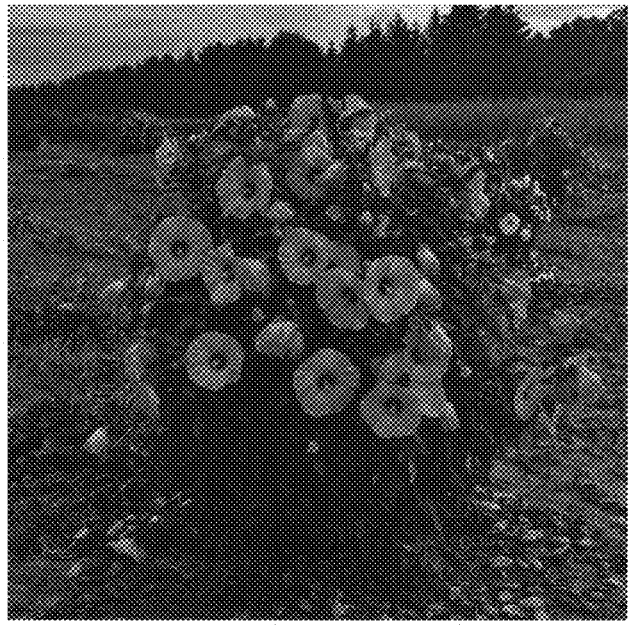
FIG. 1 shows a three-year-old plant in full flower in a trial garden.
Figure 2:
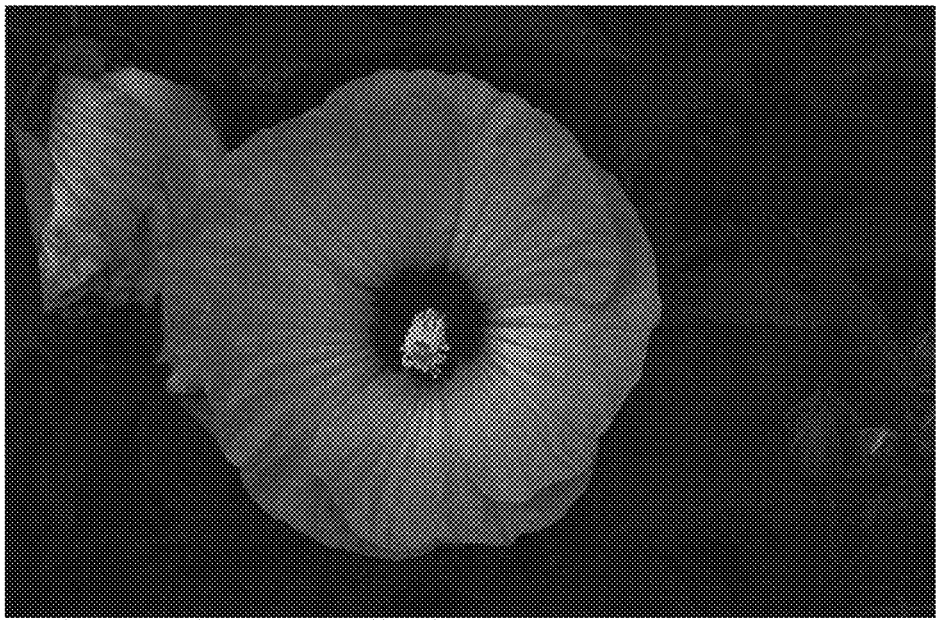
FIG. 2 shows a close-up of the flower and bud.

The following descriptions and color references are based on the 2015 edition of The Royal Horticultural Society Colour Chart except where common dictionary terms are used. The new plant, *Hibiscus* 'Candy Crush', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 12-31241, the male or pollen parent is the unreleased, non-patented, proprietary *Hibiscus* known by the breeder code 12-165-2;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 44 thick, upright, heavily-branched stems producing an upright spreading mound to about 130.0 cm tall and about 175.0 cm wide; flowering from base to top of plant with up to about 45 flowers per main stem, average flowers per stem about 33.

*Stem*.—Cylindrical, glabrous, glaucous; to about 128.0 cm tall and about 21.0 mm diameter at base, average about 122.0 cm tall and about 14.0 mm diameter at base.

*Stem color*.—Proximally nearest RHS 148C with light blush of RHS 183C, distally blend of nearest RHS 138B and RHS 183B.

*Lateral branches*.—To 9 per stem, average about 7 per stem; cylindrical, glabrous, glaucous; to about 24.0 cm long and 5.0 mm diameter at base, smaller distally.

*Lateral branch color*.—Blend of nearest RHS 138B and RHS 183B.

*Internode*.—About 12 nodes per stem below branches and 26 below single flowers; average 43 nodes per stem; internode length about 3.0 cm of unpinched plant.

*Internode color*.—Same as surrounding stem.

Foliage description: Tri-lobed to penta-lobed; alternate; coarsely and irregularly dentate; apex and side lobes acute; base rounded to nearly cordate; glabrous abaxial and adaxial; moderately to deeply incised, to less than 20.0 mm from petiole; adaxial surface lustrous when expanding, slightly lustrous when mature, abaxial surface matte; leaf blades to about 14.0 cm long and about 19.0 cm across, average blade size 12.0 cm long and 16.1 cm wide; no fragrance detected;

*Foliage color*.—Young expanding leaves — adaxial nearest RHS NN137B, abaxial nearest RHS 147B; mature leaves — adaxial nearest RHS NN137B lightly blushed in some regions with high light exposure with nearest N186C, abaxial between RHS N148A and RHS 147B.

*Veins*.—Palmate; lustrous; costate on abaxial.

*Vein color*.—Adaxial nearest RHS 160D in basal 5 mm, blushed to solid RHS 18SC distally, abaxial basally nearest RHS 145C distally heavily blushed with nearest RHS N186C.

*Petioles*.—Mostly cylindrical, proximally slightly applanate on adaxial side near base; glaucous; glabrous; to about 10.8 cm long and 5.0 mm diameter at base, average size about 7.2 cm long and 3.5 mm wide at base.

*Petiole color*.—Adaxial variable, nearest RHS 146C to blend of nearest RHS 146D and RHS 144A blushed moderately to heavily with RHS N186C in high light; abaxial nears RHS 145A in basal 4.0 cm maculate to blushed with nearest RHS N186C distally in regions of high light.

Flower description: Complete; actinomophic; mostly outward facing; rotate; lasting up to two days on plant; no fragrance detected; to about 16.0 cm across and 6.0 cm deep, decreasing distally; dark red shiny eye medium width, about 35 mm across;

*Buds one day prior to anthesis*.—Ellipsoidal with rounded apex and bluntly truncate base; sepals adpressed to petals; to about 5.7 cm long and about 2.9 cm diameter in middle.

*Bud color one day prior to anthesis*.—Exposed petal color variable, main portion between RHS 62C and RHS 62D, veins nearest RHS 64B and calyx between RHS 144A and RHS 146B.

*Epicalyx*.—Typically 10 per flower, linear; entire, glabrous, with margin micro ciliate; dull surface abaxial and adaxial; sharply acute apex and truncate base, arcuate upwards near apex; about 2.8 cm long and about 3.0 mm wide at base.

*Epicalyx color*.—Adaxial and abaxial distally nearest RHS 137B, adaxial and abaxial proximally nearest RHS 146B.

*Calyx*.—Campanulate, form star-shaped hypanthium; to about 25.0 mm deep and 5.0 cm wide at apices.

*Sepals*.—Five, acute to apiculate apex; glabrous; margin entire, edentate; abaxial and adaxial surfaces matte; about 3.2 cm long, about 1.6 cm wide at fusion, fused in basal 1.3 cm.

*Sepal color*.—Adaxial base nearest blend of RHS 144A and RHS 146B; abaxial nearest blend of RHS 144A and RHS 146B.

*Flowers*.—Solitary, up to 45 per main stem without pinching; nearly flat face; mostly outwardly facing; natural spread to about 16.0 cm across and 6.0 cm deep from stigma to base of calyx; smaller in later season.

*Flower lastingness*.—Persist for one to two days; effective for at least 5 weeks beginning late July.

*Flower fragrance*.—No detectable fragrance.

*Petals*.—Five; glabrous adaxial and abaxial; adaxial eye zone lustrous remaining distal adaxial portion and entire abaxial matte; adnate to the androecium to form a column, imbricate to about 40% overlapping at widest part (petals overlapping 40% to the petals on either side); undulation weak; palmately veined, primary veins impressed on adaxial and slightly costate abaxial; surface mostly flat; apex rounded with distinct basal claw and limb; margins entire, edentate; with about 3 to 4 mm of leading edge folded under itself.

*Petal size*.—Average about 13.0 cm across and about 9.6 cm long, claw base about 8.0 mm across (smaller in later part of flowering season).

*Petal color*.—Adaxial basal eye zone nearest RHS N186C, distally between RHS 63B and RHS 63C with veins nearest RHS 63B; abaxial basal 10 mm nearest RHS NN155D, distally between RHS 64B and RHS 64C and proximally nearest RHS 65C with veins between RHS 63B and RHS 63C.

*Flower lastingness*.—One to two days.

*Gynoecium*.—Single; partially enclosed in column. Column: glabrous and lustrous; about 4.0 cm long and about 10.0 mm across at base; with pistil exserted about 14.0 mm. Column color: variable, nearest RHS 61A near base and distally RHS NN155C. Style: micro-puberulent in region exserted above column; about 5.4 cm long, penta-furcate in about distal 6.0 mm, branch diameter about 1.2 mm; color nearest RHS 62B in exposed portion and RHS NN155D incased in column. Stigma: typically five; flattened globose, puberulent, about 3.0 mm in diameter and 1.0 mm tall; color in center nearest RHS 59D, perimeter between RHS 59B and RHS 59A. Ovary: superior; globose, longitudinally grooved; rounded to broadly acute apex and flat truncate base; about 8.0 mm across at base and about 7.0 mm tall; acute apex; color nearest RHS 16D.

*Androecium*.—Filaments: numerous, about 100, attached starting about 7 mm from base and to apex of column; to about 5.0 mm long distally and 3.5 mm long proximally, about 0.2 mm diameter; color nearest RHS N155B blushed with RHS 187D proximally and center, lighter than RHS N155B distally. Anthers: flattened reniform; dorsifixed; about 2.0 mm long and 1.0 mm across and about 0.8 mm thick; color nearest RHS 61D near perimeter and RHS 62A middle. Pollen: abundant, globose, less than 0.1 mm long; color nearest RHS 157C.

Pedicel: Cylindrical, glabrous in distal portion and micro puberulent in proximal portion; glaucous; length from base of sepal to abscission point about 2.0 cm long, from abscission point to stem node about 5.0 cm long; about 3.0 mm wide; longer on early flowers and decreasing in distal flowers; color nearest RHS 146C distal abscission point and RHS 146C with moderate blush of nearest RHS 178A proximal abscission point;

Peduncle: Cylindrical, glabrous, glaucous; to about 128.0 cm tall and about 21.0 mm diameter at base, average about 122.0 cm tall and about 14.0 mm diameter at base; flowering in upper 50 cm in center stems and nearly from the ground to apex in outer stems;

Peduncle color: Proximally nearest RHS 148C with light blush of RHS 183C, distally blend of nearest RHS 138B and RHS 183B;

Fruit: Penta-loculicidal capsule; pubescent along inner septa, glabrous outside; ellipsoidal, cuspidate apex and flattened base; about 25.0 mm long and 23.0 mm diameter; color nearest RHS 200A when mature; about 100 seeds per fruit;

Seed: Minutely hispidulous; globose; about 3.0 mm in diameter; color between RHS 200C and RHS 200D;

Resistance: *Hibiscus* 'Candy Crush' has not displayed any pest and disease resistance beyond that typical of hardy perennial *Hibiscus*. The plant grows best with plenty of moisture. Hardiness at least from USDA zone 4 through 9.

I claim:

1. A new cultivar of hardy herbaceous perennial *Hibiscus* hybrid plant named 'Candy Crush' as herein illustrated and described.

* * * * *